United States Patent

Weber et al.

[11] Patent Number: 4,581,364
[45] Date of Patent: Apr. 8, 1986

[54] 1-SUBSTITUTED-4-HYDROXYMETHYL-PYRROLIDIN-2-ONES

[75] Inventors: Karl-Heinz Weber, Gau-Algesheim; Gerhard Walther, Bingen/Rhein; Claus Schneider, Ingelheim am Rhein; Dieter Hinzen, Bingen/Rhein; Franz J. Kuhn, Gau-Algesheim; Erich Lehr, Waldalgesheim, all of Fed. Rep. of Germany

[73] Assignee: Boehringer Ingelheim KG, Ingelheim am Rhein, Fed. Rep. of Germany

[21] Appl. No.: 628,739

[22] Filed: Jul. 9, 1984

[30] Foreign Application Priority Data

Jul. 25, 1983 [DE] Fed. Rep. of Germany ....... 3326724

[51] Int. Cl.$^4$ .................. C07D 207/27; A61K 31/40
[52] U.S. Cl. .................... 514/343; 514/424; 546/281; 548/531; 548/551
[58] Field of Search ............. 548/531, 551; 546/281; 514/343, 424

[56] References Cited

U.S. PATENT DOCUMENTS 4,144,245  3/1979  Cale ................... 548/551

OTHER PUBLICATIONS

Mudzhoyan et al., Sintezy Geterotsikl, Soedin., Akad. Nauk Arm. SSR, Inst. Tonkoi Organ. Khim. 6, p. 82, 1964.

Primary Examiner—Robert Gerstl
Attorney, Agent, or Firm—Hammond & Littell, Weissenberger & Dippert

[57] ABSTRACT

Compounds of the formula

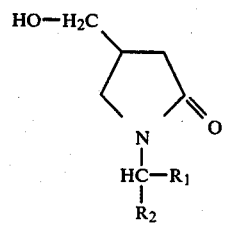

wherein
$R_1$ is hydrogen or alkyl of 1 to 4 carbon atoms; and
$R_2$ is pyridyl, phenyl or mono-, di- or tri-substituted phenyl, where the substituents are alkyl of 1 to 2 carbon atoms, alkoxy of 1 to 2 carbon atoms, fluorine, chlorine, bromine, trifluoromethyl, nitro, benzyloxy or hydroxyl.

The compounds are useful as nootropics.

7 Claims, No Drawings

1-SUBSTITUTED-4-HYDROXYMETHYL-PYR-ROLIDIN-2-ONES

This invention relates to novel 1-substituted-4-hydroxymethyl-pyrrolidin-2-ones and non-toxic acid addition salts thereof, to a method of preparing these compounds, to certain novel intermediates used in said method of preparation, to pharmaceutical compositions containing said novel pyrrolidinones as active ingredients, and to a method of using them as nootropics, that is, to alleviate or cure conditions of impaired functional capacity of the brain.

THE PRIOR ART

Structurally related nootropics, such as 1-carbamoyl-methyl-pyrrolidin-2-one (pirazetam), 1-(p-methoxybenzoyl)-pyrrolidin-2-one (anirazetam) and 1-carbamoyl-methyl-4-hydroxy-pyrrolidin-2-one (oxirazetam) are disclosed in the literature; see B. J. R. Nicolaus, Drug Development Res. 2, 464 (1982), and P. L. Paytasch, J. Amer. Chem. Soc. 72, 1415 (1950).

THE INVENTION

More particularly, the present invention relates to a novel class of compounds represented by the formula

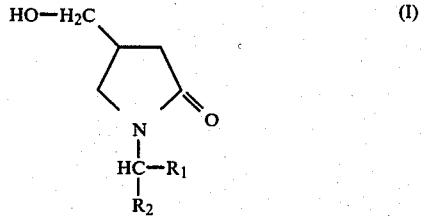

wherein $R_1$ is hydrogen or alkyl of 1 to 4 carbon atoms; and $R_2$ is pyridyl, phenyl or mono-, di- or tri-substituted phenyl, where the substituents are alkyl of 1 to 2 carbon atoms, alkoxy of 1 to 2 carbon atoms, fluorine, chlorine, bromine, trifluoromethyl, nitro, benzyloxy or hydroxyl.

A preferred subgenus thereunder is constituted by those compounds of the formula I wherein $R_1$ has the meanings previously defined, and $R_2$ is phenyl or mono-, di- or trimethoxy-substituted phenyl.

The novel compounds have a center of asymmetry and therefore occur as racemates. These racemates may be converted in the usual way, for instance by esterification with optically active acids, into the corresponding optically active esters, which are then hydrolyzed to yield the optically active forms.

The compounds embraced by formula I may be prepared by selectively reducing a pyrrolidinone-4-carboxylic acid ester of the formula

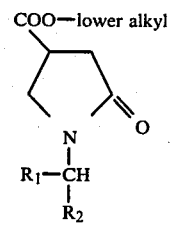

wherein $R_1$ and $R_2$ have the meanings previously defined, with a complex alkali metal borohydride.

The selective reduction is carried out with a complex alkali metal borohydride, thereby maintaining the amide function in the ring. Suitable solvents which may be used for the reduction include lower alkanols such as methanol or butanol, possibly with the addition of water. The reaction temperature is between −5° C. and the boiling point of the alcohol.

In order to prepare a compound of the formula I wherein $R_2$ is hydroxy-substituted phenyl and $R_1$ has the meanings previously defined, a compound of the formula I wherein $R_2$ is correspondingly benzyloxy-substituted phenyl is catalytically hydrogenated.

The hydrogenation is preferably carried out in the presence of an organic solvent, such as methanol, and a hydrogenation catalyst, such as palladium-on-charcoal.

The esters of the formula II used as intermediate products may be obtained from equimolar quantities of itaconic acid and a corresponding amine, possibly with subsequent esterification, according to the following reaction sequence:

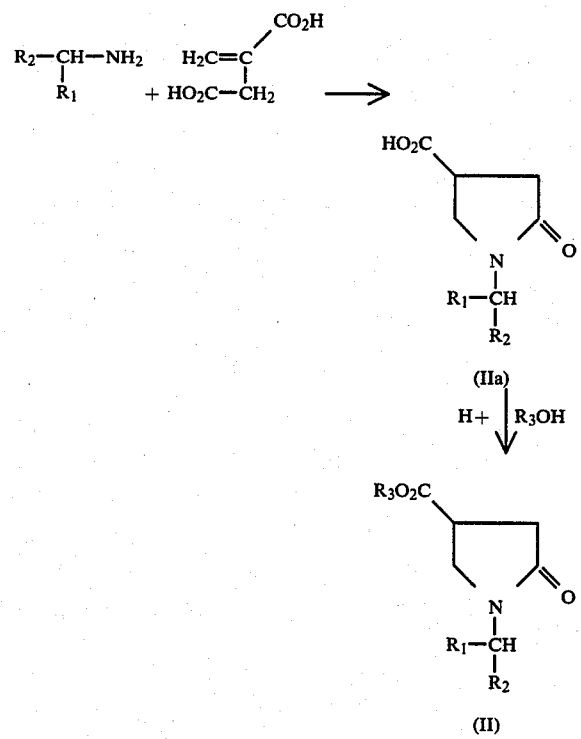

where $R_1$ and $R_2$ have the meanings previously defined, and $R_3$ is lower alkyl.

In some cases it is also possible to start with an itaconic acid ester of the formula

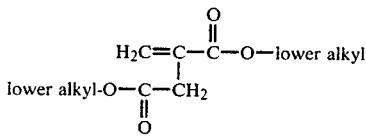

and react it directly with the desired amine to give the ester II.

The cycloaddition to the pyrrolidinone carboxylic acid may be carried out in boiling water or without a solvent, conveniently in an inert gas atmosphere, such as nitrogen, at temperatures of 100°–150° C.

The compounds embraced by formulas II and IIa are also novel. Therefore, the present invention further relates to the class of intermediates represented by the formula

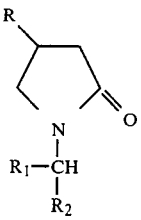

wherein
$R_1$ is hydrogen or alkyl of 1 to 4 carbon atoms,
$R_2$ is pyridyl or mono-, di- or tri-substituted phenyl where the substituents are alkyl of 1 to 2 carbon atoms, alkoxy of 1 to 2 carbon atoms, fluorine, chlorine, bromine, trifluoromethyl, nitro, benzyloxy or hydroxyl, and
R is —COOH or —COO-lower alkyl.

The following are examples of end products which may be obtained according to the process described above:
1-benzyl-4-hydroxymethyl-pyrrolidin-2-one,
1-(2-methoxybenzyl)-4-hydroxymethyl-pyrrolidin-2-one,
1-(3-methoxybenzyl)-4-hydroxymethyl-pyrrolidin-2-one,
1-(4-methoxybenzyl)-4-hydroxymethyl-pyrrolidin-2-one,
1-(3,4-dimethoxybenzyl)-4-hydroxymethyl-pyrrolidin-2-one,
1-(3,4,5-trimethoxybenzyl)-4-hydroxymethyl-pyrrolidin-2-one,
1-(4-methylbenzyl)-4-hydroxymethyl-pyrrolidin-2-one,
1-(4-chlorobenzyl)-4-hydroxymethyl-pyrrolidin-2-one,
1-(2-chlorobenzyl)-4-hydroxymethyl-pyrrolidin-2-one,
1-(4-fluorobenzyl)-4-hydroxymethyl-pyrrolidin-2-one,
1-(3-trifluoromethylbenzyl)-4-hydroxymethyl-pyrrolidin-2-one,
1-(3-hydroxy-4-methoxybenzyl)-4-hydroxymethyl-pyrrolidin-2-one,
1-(3-methoxy-4-hydroxybenzyl)-4-hydroxymethyl-pyrrolidin-2-one,
1-(2-methyl-4-chlorobenzyl)-4-hydroxymethyl-pyrrolidin-2-one,
1-(α-methylbenzyl)-4-hydroxymethyl-pyrrolidin-2-one,
1-(α-methyl-4-methoxybenzyl)-4-hydroxymethyl-pyrrolidin-2-one,
1-pyridyl-(2)-methyl-4-hydroxymethyl-pyrrolidin-2-one,
1-pyridyl-(3)-methyl-4-hydroxymethyl-pyrrolidin-2-one,
1-pyridyl-(4)-methyl-4-hydroxymethyl-pyrrolidin-2-one, and
1-(4-hydroxybenzyl)-4-hydroxymethyl-pyrrolidin-2-one.

The following examples illustrate the present invention and will enable others skilled in the art to understand it more completely. It should be understood, however, that the invention is not limited solely to the particular examples given below.

EXAMPLE 1

1-(3,4-Dimethoxybenzyl)-4-hydroxymethyl-pyrrolidin-2-one 8.0 g of 1-(3,4-dimethoxybenzyl)-4-ethoxycarbonyl-pyrrolidin-2-one were dissolved in 100 ml of methanol. Over a period of 20 minutes, at 0°–10° C., a solution of 2.8 g of sodium borohydride in 30 ml of water was added dropwise, while mechanically stirring, and the mixture was stirred for 5 hours more at 0°–10° C. The excess borohydride was then carefully decomposed by the addition of glacial acetic acid up to a pH of 5 and until the development of gas had ceased, and the methanol was distilled off in vacuo. Some water was added, and the reaction product was taken up in methylene chloride. The methylene chloride phase was then washed with water, dried and evaporated. The residue was chromatographed on silica gel (eluant: methylene chloride/methanol 98:2). Finally, 4.8 g (62% of theory) of the title compound were obtained from the eluate.

Melting point: 78°–79° C.

The starting ester was obtained as follows:

(a) A mixture of 6.0 g (46 mmols) of itaconic acid and 7.7 g (46 mmols) of 3,4-dimethoxybenzylamine was heated at 130° C. for 2 hours in a nitrogen atmosphere. After cooling to about 100° C., 70 ml of 10% sodium hydroxide were added to the viscous reaction mixture, while mechanically stirring, and the resulting mixture was then cooled to room temperature. In order to remove any insoluble matter, the sodium salt solution was extracted with 50 to 100 ml of ethyl acetate, and the aqueous phase was acidified with dilute hydrochloric acid. The oil precipitated thereby was taken up in methylene chloride, and the methylene chloride phase was dried and concentrated by evaporation. The residue crystallized when ether was added. 8.7 g (68% of theory) of 1-(3,4-dimethoxybenzyl)-4-carboxy-pyrrolidin-2-one were obtained. Melting point: 176°–178° C.

(b) 8.6 g (30 mmols) of the acid were dissolved in 120 ml of absolute ethanol, and the solution was refluxed for 2 hours while dry HCl gas was constantly introduced. Then the excess alcohol was distilled off in vacuo, and the residue was adjusted to pH 8 with a 30% sodium carbonate solution, while cooling. After extracting with methylene chloride, washing the extract solution with water and drying it, and evaporating the solvent, about 10 g of 1-(3,4-dimethoxybenzyl)-4-ethoxycarbonyl-pyrrolidin-2-one were obtained in the form of a yellow oil which was used in its crude form.

The ester obtained in (b) may also be prepared by the following method:

A mixture of 10 g (0.064 mol) of dimethyl itaconate and 7.7 g (0.064 mol) of α-phenylethylamine was stirred for 2 hours at 120° to 130° C. in a nitrogen atmosphere. The reaction product was then fractionally distilled at 150°–155° C. and at 0.1 Torr.

9.5 g (60% of theory) of a light-colored oil were obtained, which was used as such for the selective reduction.

EXAMPLE 2

1-(p-Fluorobenzyl)-4-hydroxymethyl-pyrrolidin-2-one 4.0 g (16 mol) of 1-(p-fluorobenzyl)-4-ethoxy-carbonyl-pyrrolidin-2-one were dissolved in 60 ml of tertiary butanol, and 1.5 g of sodium borohydride were added. The mixture was heated to reflux temperature and, over a period of one hour, 12 ml of dry methanol were gradually added thereto.

After another hour the reaction mixture was concentrated by evaporation in vacuo. The residue was diluted with water, and the title compound was extracted with methylene chloride and worked up as described in Example 1. The yield of pure title compound was 2.5 g, melting point 121°–122° C., which is 72% of theory based on the crude ester.

The ester was obtained as follows:

7 g (54 mmols) of itaconic acid and 6.8 g (54 mmols) of 4-fluorobenzylamine were refluxed with 50 ml of water for 3 hours. The mixture was then made distinctly alkaline with 10% sodium hydroxide, the water-insoluble components were extracted with ethyl acetate, and the aqueous phase was acidified with HCl. Further working up was carried out as in Example 1. Light-brown crystals of the corresponding carboxylic acid, melting point 152°–153° C., were obtained which were esterified by the method described in Example 1.

The end products listed in the following Table were obtained by the process described above via the carboxylic acid intermediate specified:

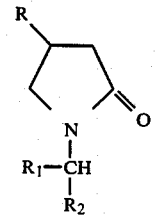

| End products | | | | | Intermediates | |
|---|---|---|---|---|---|---|
| R | $R_1$ | $R_2$ | M.p. °C. | B.p. 0.1° C. | R | M.p. °C. |
| —CH₂—OH | H | (phenyl) | 63–64 | | CO₂H | 144–146 |
| —CH₂—OH | H | (4-OCH₃-phenyl) | 188–190 | | CO₂H | 158–159 |
| —CH₂—OH | H | (3-OCH₃-phenyl) | 165–168 | | CO₂H | 112–113 |
| —CH₂—OH | H | (4-CH₃-phenyl) | 165–168 | | CO₂H | 156–157 |
| —CH₂—OH | H | (4-Cl-phenyl) | 77–78 | 162–165 | CO₂H | 160–161 |
| —CH₂—OH | H | (3-CF₃-phenyl) | | 95–96 | CO₂H | |
| —CH₂—OH | CH₃ | (phenyl) | | 146–147 | CO₂H | 180–181 |
| —CH₂—OH | CH₃ | (4-OCH₃-phenyl) | | 170–172 | CO₂H | 165–166 |

-continued

| R | R$_1$ | R$_2$ | M.p. °C. | B.p. 0.1° C. | R | M.p. °C. |
|---|---|---|---|---|---|---|
| —CH$_2$—OH | H | 3-pyridyl | | 178–182 | CO$_2$H | |
| —CH$_2$—OH | H | 4-pyridyl | 79–80 | | CO$_2$H | |
| —CH$_2$—OH | H | 2-pyridyl | | 160–163 | CO$_2$H | |
| —CH$_2$—OH | H | phenyl with O—CH$_2$—C$_6$H$_5$ and OCH$_3$ | Oil | | | |
| —CH$_2$—OH | H | phenyl with OCH$_3$ and O—CH$_2$—C$_2$H$_5$ | Oil | | | |
| —CH$_2$—OH | H | phenyl with O—CH$_2$—C$_6$H$_5$ | 104–105 | | | |
| —CH$_2$—OH | H | phenyl with OH | 150–152 | | | |
| —CH$_2$—OH | H | phenyl with OH and OCH$_3$ | 99–101 | | | |
| —CH$_2$—OH | H | phenyl with OCH$_3$ and OH | 128 | | | |
| —CH$_2$—OH | H | phenyl with Cl | 84–86 | | | |

The compounds of the present invention, that is, those embraced by formula I, have useful pharmacodynamic properties. More particularly, they exhibit nootropic activity in warm-blooded animals.

The novel pyrrolidinone derivatives of this invention were tested in animal experiments with regard to their activity of curing or alleviating conditions of impaired cerebral performance.

In tolerance tests, which were carried out as a guide, the compounds show no acute toxicity (14 days observation) when administered to mice in doses of up to 2 g/kg (single oral administration). In animal experiments they show excellent effects on spontaneous cognitive performance, such as experimentally impaired learning and memory processes. In tests with a restriction of the short term memory or inhibition of the transition from contents of the short term memory to the long term memory, but the administration of a muscarinic cholinergic antagonist [scopolamine 0.6 mg/kg i.p.; see also Psychopharmacology 78, 104-111 (1982)], the compounds are capable of counteracting or even curing this pharmacologically induced cerebral insufficiency.

The learning capacities of rats in an active avoidance training [J. Pharmacol. Methods, 8, 155-163 (1983)] are improved as is their spontaneous habituation or exploring orientation activity in a new environment.

The novel pyrrolidinone derivatives were compared in their activity with pyrrolidinones of different structures which are already used as drugs in human medicine (pirazetam) or are at present undergoing clinical trials (anriazetam) with regard to cerebral insufficiency or organic brain psychodrome, post-traumatic and alcoholic brain damage, etc.

The novel compounds are clearly superior to the above-mentioned known substances both in their effective dosage and also in the improvement in performance obtained in the animal experiments.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 0.7 to 2.8 mgm/kg body weight, preferably 1.0 to 2.1 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 3

Tablets

The tablet composition is compounded from the following ingredients:

| | |
|---|---|
| 1-(3,4-Dimethoxybenzyl)-4-hydroxymethyl-pyrrolidin-2-one | 100 parts |
| Lactose (powdered) | 140 parts |
| Corn starch | 240 parts |
| Polyvinyl pyrrolidone | 15 parts |
| Magnesium stearate | 5 parts |
| | 500 parts |

Preparation:

The finely ground active ingredient, lactose and some of the corn starch are mixed together. The mixture is screened, then moistened with a solution of polyvinyl pyrrolidone in water, kneaded, moist-granulated and dried. The granulate, the remaining corn starch and the magnesium stearate are screened and mixed together. The mixture is compressed into 500 mg-tablets of a suitable size and shape, each of which contains 100 mg of the active ingredient.

EXAMPLE 4

Tablets

The tablet composition is compounded from the following ingredients:

| | |
|---|---|
| 1-(3,4-Dimethoxybenzyl)-4-hydroxymethyl-pyrrolidin-2-one | 80 parts |
| Corn starch | 190 parts |
| Lactose | 55 parts |
| Microcrystalline cellulose | 35 parts |
| Polyvinyl pyrrolidone | 15 parts |
| Sodium carboxymethyl starch | 23 parts |
| Magnesium stearate | 2 parts |
| | 400 parts |

Preparation:

The finely ground active substance, some of the corn starch, lactose, microcrystalline cellulose and polyvinyl pyrrolidone are mixed together, the mixture is screened and processed with the remaining corn starch and water to form a granulate which is dried and screened. The sodium carboxymethyl starch and the magnesium stearate are added, and the mixture is compressed into 400 mg-tablets of a suitable size and shape, each of which contains 80 mg of the active ingredient.

EXAMPLE 5

Injectable solution

| | |
|---|---|
| (a) Ampule with solution of active ingredient | |
| 1-benzyl-4-hydroxymethyl-pyrrolidin-2-one | 100 mg |
| Polyethylene glycol q.s. ad | 5 ml |
| (b) Ampule with diluent | |
| Double-distilled water | 5 ml |

Before injection, the diluent is added to the contents of the ampule containing the active ingredient solution. 10 ml of an injectable solution are obtained containing 100 mg of the active ingredient.

EXAMPLE 6

Injectable solution

| | |
|---|---|
| (a) Ampule with solution of active ingredient | |
| 1-(4-methoxybenzyl)-4-hydroxymethyl-pyrrolidin-2-one | 120.0 mg |
| Glycofurol q.s. ad | 3.5 ml |
| (b) Diluent | |
| Sodium chloride | 67.5 mg |
| Double-distilled water q.s. ad | 6.5 ml |

Before injection, the diluent is added to the contents of the ampule containing the active ingredient solution. 10 ml of an injectable solution are obtained containing 120 mg of the active ingredient.

EXAMPLE 7

Injectable solution

| The solution is compounded from the following ingredients: | |
|---|---|
| 1-Pyridyl-(4)-methyl-4-hydroxymethyl-pyrrolidon-2-one | 80 parts |
| Sodium pyrosulfite | 20 parts |
| Disodium salt of ethylenediamine-tetra-acetic acid | 8 parts |
| Sodium chloride | 50 parts |
| Double-distilled water q.s. ad | 1000 parts |

Preparation:

The active ingredient and the excipients are dissolved in a sufficient quantity of water, and the solution is diluted to the desired concentration with the required amount of water. The solution is filtered and filled into 1 ml ampules under aseptic conditions. Finally, the ampules are sterilized and sealed. Each ampule contains 80 mg of the active ingredient.

Any one of the other compounds embraced by formula I may be substituted for the particular active ingredient in Examples 3 through 7. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

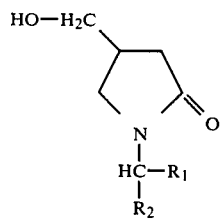

wherein
$R_1$ is hydrogen or alkyl of 1 to 4 carbon atoms; and
$R_2$ is pyridyl, phenyl or mono-, di- or tri-substituted phenyl, where the substituents are alkyl of 1 to 2 carbon atoms, alkoxy of 1 to 2 carbon atoms, fluorine, chlorine, bromine, trifluoromethyl, nitro, benzyloxy or hydroxyl.

2. A compound of claim 1, where
$R_1$ is hydrogen or alkyl of 1 to 4 carbon atoms, and
$R_2$ is phenyl or mono-, di- or trimethoxy-substituted phenyl.

3. The compound of claim 1 which is 1-benzyl-4-hydroxymethyl-pyrrolidin-2-one.

4. The compound of claim 1 which is 1-(4-methoxybenzyl)-4-hydroxymethyl-pyrrolidin-2-one.

5. The compound of claim 1 which is 1-(3,4-dimethoxybenzyl)-4-hydroxymethyl-pyrrolidin-2-one.

6. A nootropic pharmaceutical composition consisting essentially of an inert pharmaceutical carrier and an effective nootropic amount of a compound of claim 1.

7. The method of alleviating conditions of impaired cerebral performance in a warm-blooded animal in need thereof, which comprises perorally or parenterally administering to said animal an effective nootropic amount of a compound of claim 1.

* * * * *

UNITED STATES PATENT AND TRADEMARK OFFICE
CERTIFICATE OF CORRECTION

PATENT NO. : 4,581,364
DATED : Apr. 8, 1986
INVENTOR(S) : KARL-HEINZ WEBER ET AL.

It is certified that error appears in the above-identified patent and that said Letters Patent is hereby corrected as shown below:

Column 7, 5th formula: " 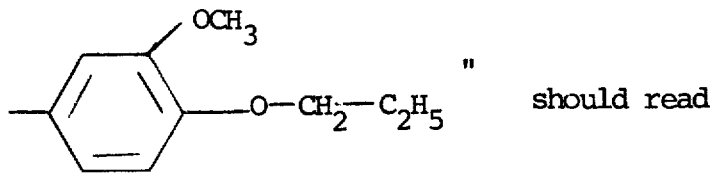 " should read

-- 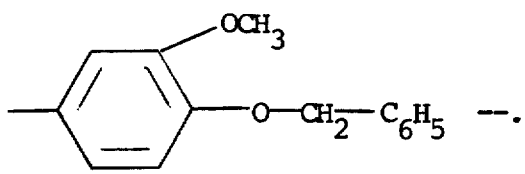 --.

Column 9, line 2: "but" should read -- by --.

Signed and Sealed this

Twelfth Day of August 1986

[SEAL]

Attest:

DONALD J. QUIGG

Attesting Officer   Commissioner of Patents and Trademarks